(12) United States Patent
Martin et al.

(10) Patent No.: US 8,534,911 B2
(45) Date of Patent: Sep. 17, 2013

(54) INSTRUMENT CASE ASSEMBLIES

(76) Inventors: Jason Perry Martin, Lake Oswego, OR (US); Michael D. Prstojevich, Portland, OR (US)

( * ) Notice: Subject to any disclaimer, the term of this patent is extended or adjusted under 35 U.S.C. 154(b) by 149 days.

(21) Appl. No.: 11/676,266

(22) Filed: Feb. 16, 2007

(65) Prior Publication Data
US 2008/0089185 A1  Apr. 17, 2008

Related U.S. Application Data

(60) Provisional application No. 60/829,524, filed on Oct. 13, 2006.

(51) Int. Cl.
*A45C 11/10* (2006.01)

(52) U.S. Cl.
USPC .......................................... 368/283; 368/281

(58) Field of Classification Search
USPC ................ 368/281, 283, 286, 294, 276, 277, 368/297, 300, 295, 296, 288, 292, 293, 319, 368/307
See application file for complete search history.

(56) References Cited

U.S. PATENT DOCUMENTS

| | | | | |
|---|---|---|---|---|
| 1,313,636 A | * | 8/1919 | Larkin | 368/286 |
| 3,635,012 A | * | 1/1972 | Grohoski | 368/307 |
| 4,089,158 A | * | 5/1978 | Wenger | 368/216 |
| 4,837,756 A | * | 6/1989 | Hartman et al. | 368/286 |
| 5,943,302 A | * | 8/1999 | Fanshaw | 368/276 |

\* cited by examiner

*Primary Examiner* — Renee S Luebke
*Assistant Examiner* — Jason Collins
(74) *Attorney, Agent, or Firm* — Mersenne Law LLC

(57) ABSTRACT

An instrument case assembly may include an instrument case having a face, a back, and at least one side extending between the face and the back about a perimeter of the case. The face may include a crystal held by a perimetrical bezel. In some aspects, a pair of strap brackets may be removably coupled to the at least one side at substantially opposite perimetrical regions of the case. In some aspects, a crystal guard may be coupled to the case.

6 Claims, 7 Drawing Sheets

INSTRUMENT CASE ASSEMBLIES

CROSS-REFERENCE TO RELATED APPLICATIONS

This application claims the benefit of priority of U.S. provisional application No. 60/829,524, filed on Oct. 13, 2006, the contents of which are incorporated herein by reference in their entirety.

TECHNICAL FIELD

The present disclosure is directed to instrument cases. More particularly, the present disclosure relates to crystal guards that incorporate a protector, or guard portion, located at the perimeter of the crystal of an instrument case and being so formed as to isolate the crystal from abrasive contact or impact.

BACKGROUND

The crystal of a watch or other instrument can be formed of mineral crystal, gemstone crystal, or synthetic plastic. The protection of the crystal of the watch becomes extremely important when, as in many high-fashion or mass-produced watches, the crystal is fabricated from synthetic plastics and, thus, is more prone to be readily abraded or scratched, thus obscuring portions of the watch face and, in addition, detracting from the decorative effect of the watch. Some conventional devices, for example, U.S. Pat. No. 4,837,756, have been designed to protect a watch crystal.

Some conventional devices include a centrally-located guard member that prevents reading of the watch hands when they are located in the central position on the watch and cover some portion of the watch hands or indicia.

Some conventional devices include metal shells that cover the face of the watch, making the reading of the time, as indicated by hands of the watch, extremely difficult. These metal shells are intended to convert a pocket watch into a wrist watch, but do not afford any protection to the crystal of the watch since they are disposed outwardly of the crystal and are located, generally, in the plane of the crystal.

It may be desirable to provide a crystal protector that does not obscure portions of an instrument necessary for reading the time and/or other types of indicia on the face of the instrument.

SUMMARY

According to various aspects of the disclosure, a case assembly may comprise a case having a face, a back, and at least one side extending between the face and the back about a perimeter of the case. The face may include a crystal held by a perimetrical bezel. A pair of strap brackets may be removably coupled to the at least one side at substantially opposite perimetrical regions of the case.

In accordance with some aspects of the disclosure, a case assembly may comprise a case having a face, a back, and at least one side extending between the face and the back about a perimeter of the case. The face may include a crystal held by a perimetrical bezel. A crystal guard may be coupled to the case. The crystal guard may have a substantially central opening configured to permit viewing of a substantially center region of the face. The crystal guard may further include a plurality of openings located outward of the central opening and spaced about a periphery of the face. The plurality of openings may be configured to correspond with indicia on the face.

According to some aspects of the disclosure, a case assembly may comprise a case having a face, a back, and at least one side extending between the face and the back about a perimeter of the case. The face may include a crystal held by a perimetrical bezel. A crystal guard may be coupled to the case. The crystal guard may have a portion extending in a direction from the face over the side of the case, wherein the portion includes a sleeve extending outward from the side of the case. The assembly may further include a fastener slidably coupled with the sleeve. The fastener may be configured to be received by the bore to secure the crystal guard to the case.

BRIEF DESCRIPTION OF THE DRAWINGS

The disclosed subject matter of the present application will now be described in more detail with reference to exemplary embodiments of the apparatus, given only by way of example, and with reference to the accompanying drawings, in which.

DETAILED DESCRIPTION

Figure 1:
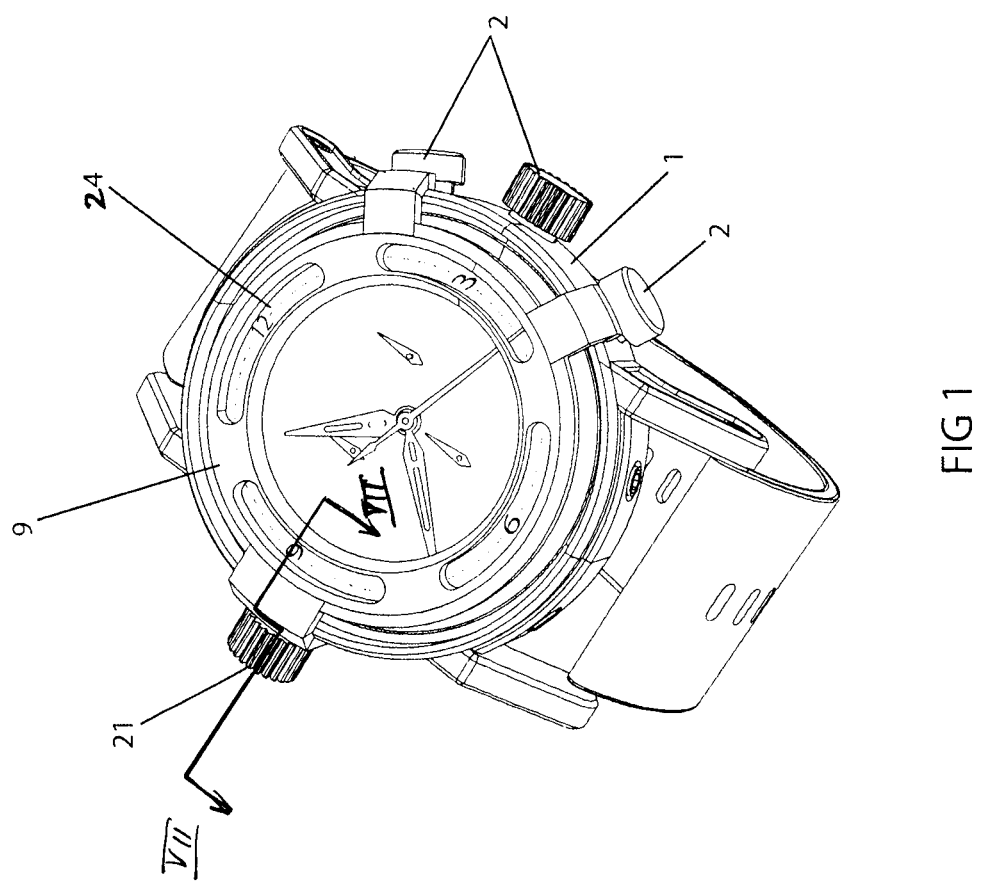
FIG. 1 is a perspective view of a watch having an assembled watch case and exemplary crystal guard in accordance with various aspects of the disclosure.

Referring to the drawing figures, like reference numerals designate identical or corresponding elements throughout the several figures.

Referring now in detail to the drawings, an exemplary instrument case 1 such as, for example, a watch case, consistent with this disclosure may comprise a number of interrelated elements as shown in FIGS. 1-5. With reference to FIG. 1, a crystal guard 9, for example, an annular, perimetrical crystal guard, can be removably coupled to a top side of the instrument case 1. It should be noted that the guard can be any shape as long as it overlies at least a portion of the instument's periphery. According to various aspects of the disclosure, the instrument case 1 may comprise a case for any known instrument including, but not limited to, calculators, music and/or video devices, and/or devices that measure and/or display weather information, various body attributes such as heart rate, pulse, etc., and/or workout information such as distance walked/run, calories burned, etc.

Figure 7:
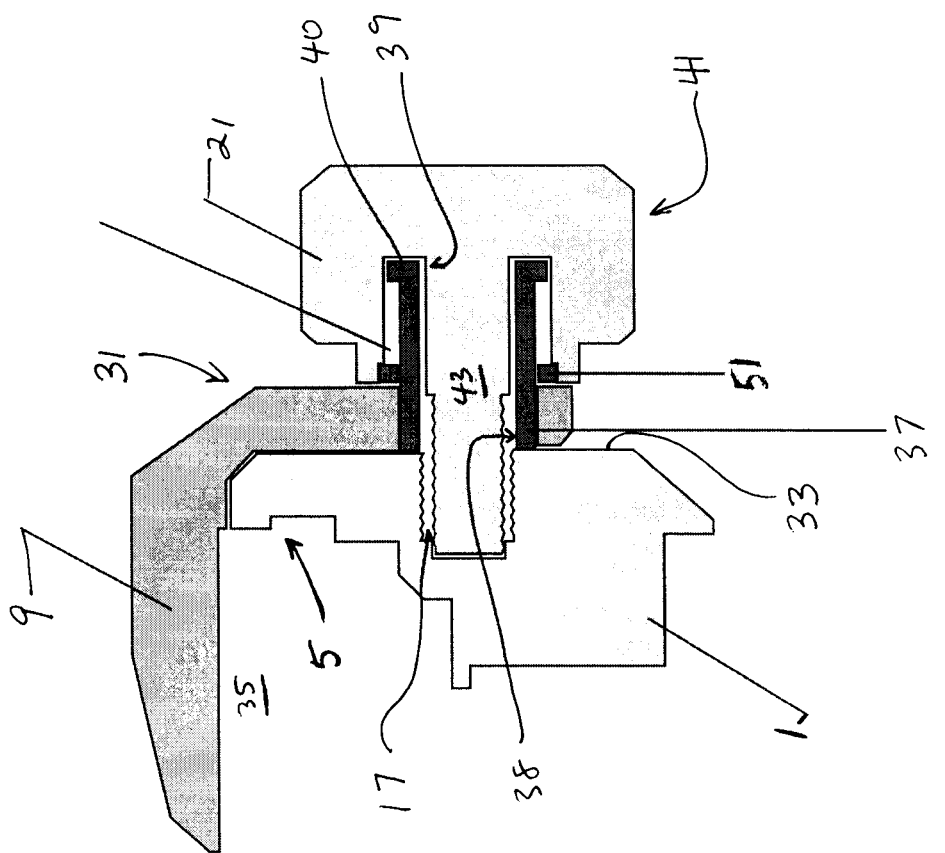
FIG. 7 is cross-sectional view along line VII-VII of FIG. 1.

The crystal guard 9 may be configured to protect a crystal 12 held by a perimetrical bezel 4 (FIG. 7). The crystal 12 may comprise mineral crystal, gemstone crystal, or synthetic plastic.

Figure 2:
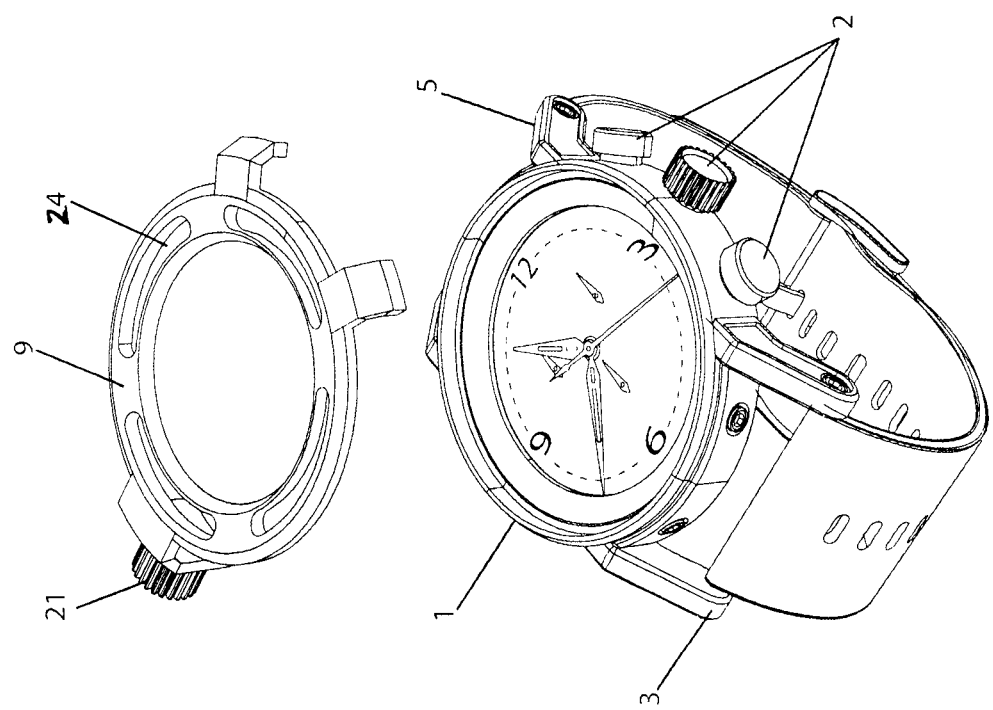
FIG. 2 is a perspective view of the watch case and the exemplary crystal guard of FIG. 1 with the crystal guard removed.
Figure 3:
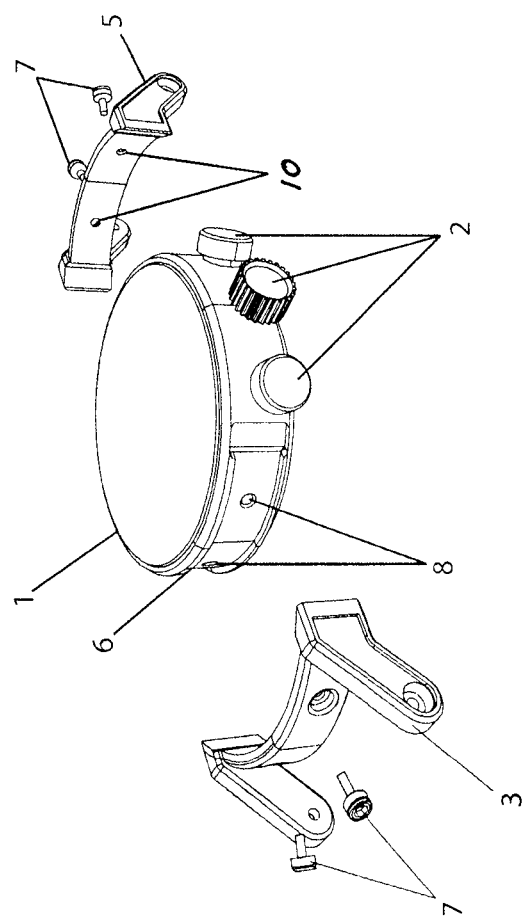
FIG. 3 is an exploded view of a watch case and exemplary strap brackets in accordance with various aspects of the disclosure.

According to one aspect of the disclosure, watch movement control buttons 2 can be mounted on a side of the case 1 between two strap brackets 3 and 5 (FIG. 2). Referring now to FIG. 3, the strap brackets 3 and 5 can be removably mounted to substantially opposing sides of the case 1. The removable strap brackets 3 and 5 may permit a user to easily modify the appearance of a watch, replace a worn or broken strap, and/or fix a broken bracket. It should be appreciated that the instrument case 1 may comprises various other types of control buttons 2 for instruments other than watches.

The case 1 may include recessed areas 6 on opposing sides of the case 1 where strap brackets 3 and 5 can be mounted. One or more fastening elements 7 can extend through a corresponding number of openings 10 on the strap brackets 3 and 5 and terminate in openings 8 in the case 1 to securely and removably couple the strap brackets 3 and 5 to the case 1. According to various aspects, the fastening elements 7 may comprise screw-type fasteners, although it should be appreciated that other types of fasteners may be utilized. The recessed areas of the case limit rotational movement of the brackets 3 and 5 thereby avoiding any sheering force on the fastening elements 7.

Figure 4:
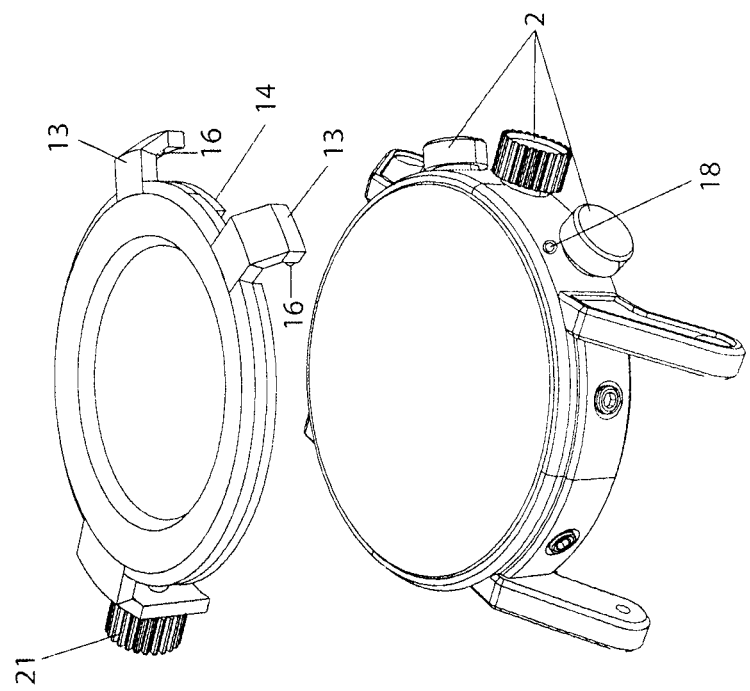
FIG. 4 is a perspective view of the watch case and exemplary crystal protector of FIG. 1.

As shown in FIG. 4, the crystal guard 9 can be mounted to the top side of the case 1 to prevent the crystal 12 from being scratched. The crystal guard 9 may have an annular ring portion that covers the interface between the instrument case 1 and the crystal 12. According to various aspects of the disclosure, the crystal guard 9 can have a height of at least 0.1 mm in a direction perpendicular to the crystal 9. According to some aspects, the height of the crystal guard 9 may be greater than 0.5 mm to provide additional protection of the crystal. For example, according to various aspects the crystal guard 9 may have a height between about 0.1 mm and about 5.0 mm. In some aspects, the height of the crystal guard 9 may be about 0.5 mm to about 1.0 mm.

According to various aspects of the disclosure, the crystal guard 9 can have a damping member 14 on the underside of the annular ring portion that faces the crystal 12. The damping member 14 can prevent shock and provide scratch protection for the crystal 12. The damping member 14 may be formed, for example, from rubber, plastic, or textile material.

In some aspects of the disclosure, the crystal guard 9 can include arms 13 extending off the annular ring. According to various aspects, the arms 13 can be substantially rigid. The arms 13 may have detents 16 at their extremity that lock onto spring biased balls 18 located in the instrument case 1. In some aspects, the spring biased balls can be located in the arms and the detents can be located in the case.

Figure 5:
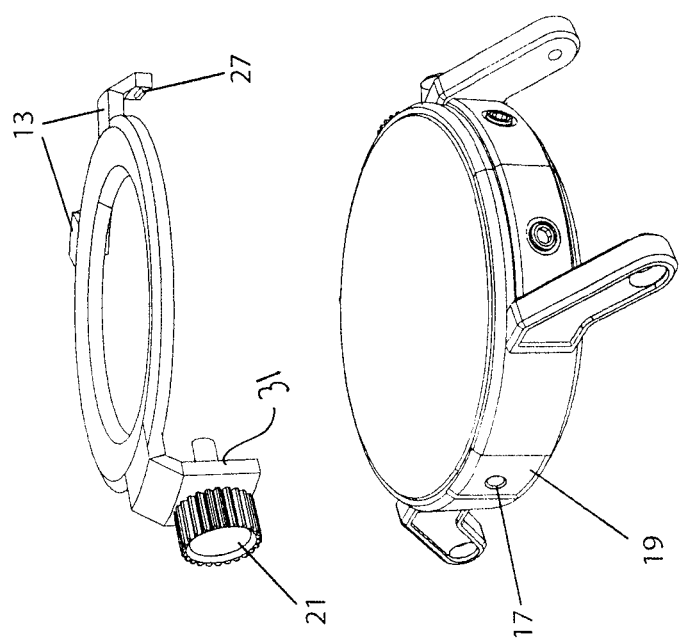
FIG. 5 is a perspective view of a watch case and an exemplary crystal protector in accordance with various aspects of the disclosure.
Figure 6:
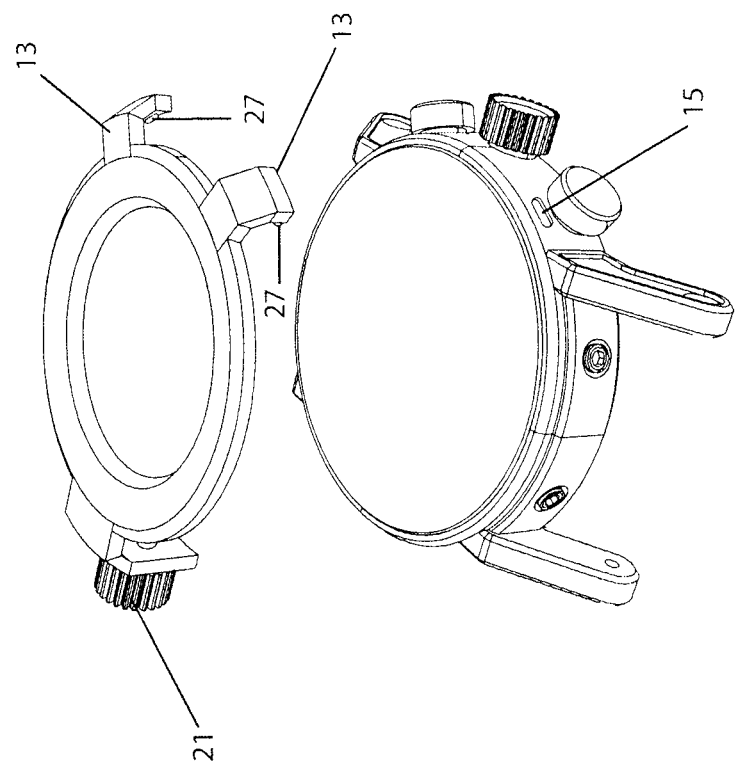
FIG. 6 is an alternate perspective view of the watch case and exemplary crystal guard of FIG. 5.

Referring now to FIGS. 5 and 6, the arms 13 of the crystal guard 9 can include tabs 27 that engage slots 15 in the instrument case 1. The crystal guard may include a screw crown 21 extending from the annular ring portion of the crystal guard 9. The screw crown 21 can fit into a mating recess 17, or bore, on the case 1 to removably secure the crystal protector 9 to the instrument case 1. An arm 31 that holds the screw crown 21 can seat in a groove 19 on the watch case 1, as can be seen in FIG. 5.

Referring now to FIG. 7, the side 33 of the case 1 may include bore 17. The crystal guard 9 may be coupled to the case 1 via arm 31 extending in a direction from the face 35 over the side 33 of the case 1. The arm 31 may include a sleeve 37 extending outward from the side 33 of the case 1.

A fastener 41 may be slidably coupled with the sleeve 37. For example, the sleeve 37 may comprise a first end 38 proximate the side 33 of the case 1 and a second end 39 spaced from the side 33 of the case 1. The fastener may comprise crown 21 extending about the second end 39 of the sleeve 37 and a pin 43 extending through the sleeve 37 from the second end 39 to the first end 38 and into the bore 17. The bore 17 may be configured to receive the pin 43 of the fastener 41 so as to secure the crystal guard 9 to the case 1. The bore 17 and the fastener 41 may be connected via a screw fit, snap fit, interference (friction) fit, or the like.

As shown in FIG. 7, a washer 51 may be coupled with the crown, and the second end 39 of the sleeve 37 may comprise a flange 40. The washer 51 may be configured to cooperate with the flange 40 to prevent removal of the fastener 41 from the crystal guard 9 my limiting movement of the fastener 41 in a direction away from the case 1.

Referring again to FIGS. 1-2, in some aspects of the disclosure, the crystal guard 9 may have openings 24 formed through the thickness of the annular perimetrical ring portion. The openings 24 can allow a viewer to better see the watch face and, for example, any numbers or indicia printed around the periphery of the watch face. The openings 24 need not be elongated slots as shown in FIG. 1, but could be formed of any shape so long as they are formed through the thickness of the ring portion.

It will be apparent to those skilled in the art that various modifications and variations can be made in the instrument case assemblies of the present disclosure without departing from the scope of the disclosure. Other embodiments of the disclosure will be apparent to those skilled in the art from consideration of the specification and practice of the subject matter disclosed herein. It is intended that the specification and examples be considered as exemplary only.

What is claimed is:

1. An instrument case assembly, comprising:
an instrument case having a face, a back, and at least one side extending between the face and the back about a perimeter of the case, the face comprising a crystal held by a perimetrical bezel; and
a crystal guard detachably secured to the case, said crystal guard having a substantially central opening configured to permit viewing of a substantially center region of the face, said crystal guard further including a plurality of openings located outward of the central opening and spaced about a periphery of the face, the plurality of openings being configured to correspond with indicia on the face.

2. The instrument case assembly of claim 1, wherein the instrument case comprises a watch case.

3. The instrument case assembly of claim 1, wherein the crystal comprises one of mineral crystal. gemstone crystal, and synthetic plastic.

4. The instrument case assembly of claim 1, further comprising at least one moveable member beneath the crystal, said moveable member being visible through said central opening.

5. The instrument case assembly of claim 1, wherein the indicia indicate a plurality of hours that facilitate determination of time.

6. The instrument case assembly of claim 1, wherein the crystal guard comprises at least one arm extending from the face over the at least one side, one of the arm and the side comprising a spring-biased member and the other arm and the side comprising a detent, the spring-biased member and the detent cooperating to couple the crystal guard with the case.

* * * * *